United States Patent [19]

De Leon et al.

[11] Patent Number: 4,846,844

[45] Date of Patent: Jul. 11, 1989

[54] ANTIMICROBIAL COATED IMPLANTS

[75] Inventors: José De Leon, Canovanas, P.R.; Thomas H. Ferguson, Greenfield; Daniel S. Skinner, Jr., Indianapolis, both of Ind.

[73] Assignee: Eli Lilly and Company, Indianapolis, Ind.

[21] Appl. No.: 91,075

[22] Filed: Aug. 31, 1987

[51] Int. Cl.$^4$ ............................................. A61F 2/54
[52] U.S. Cl. ........................................ 623/66; 623/11;
128/DIG. 21; 424/425; 427/2; 514/179;
604/890.1
[58] Field of Search .................. 128/DIG. 21, 1 R;
424/425; 427/2; 514/179; 604/890, 891, 892;
623/11, 13, 66

[56] References Cited

U.S. PATENT DOCUMENTS

| | | | |
|---|---|---|---|
| 3,295,950 | 1/1967 | Blouin et al. | 71/64 |
| 3,580,715 | 5/1971 | Dilday | 71/28 |
| 3,697,245 | 10/1972 | Dilday | 71/28 |
| 4,003,312 | 1/1977 | Gunther | 101/466 |
| 4,126,722 | 11/1978 | Murphy | 29/132 |
| 4,191,741 | 3/1980 | Hudson et al. | 424/78 |
| 4,248,992 | 2/1981 | Takago | 427/2 |
| 4,360,563 | 11/1982 | Stengle | 428/323 |
| 4,500,339 | 2/1985 | Young et al. | 427/2 |
| 4,581,028 | 4/1986 | Fox, Jr. et al. | 623/2 |
| 4,592,920 | 6/1986 | Murtfeldt | 427/2 |

FOREIGN PATENT DOCUMENTS

| | | |
|---|---|---|
| 184465 | 6/1986 | European Pat. Off. . |
| 191789 | 8/1986 | European Pat. Off. . |
| 222498A1 | 3/1984 | German Democratic Rep. . |
| 59-044310 | 3/1984 | Japan . |
| 1412970 | 1/1974 | United Kingdom . |
| 2136688 | 9/1984 | United Kingdom . |
| 2167662 | 6/1986 | United Kingdom ................ 424/425 |

OTHER PUBLICATIONS

Abstract of GB-2160792 published Jan. 2, 1986, for Fuchs.
Abstract of BE-848892 published Mar. 16, 1977, for Kockums Chem.
Abstract of JP-49101521 published Sep. 25, 1974, for Toyo Brewing KK.
Mullison (Editor), *The Bulletin*, "Antibiotics and Insecticides Administered in Silastic Rubber Implants", p. 1, (Jan. 1968).
"Antibiotic Coating-A Possible Prophylaxis Against Bacterial Colonization on Plastic Implants", Straube E.; Naumann, G., Klein, H., Klein, F., *Z. Antimikrob. Antineoplast Chemother.*, 1985, 3(3-4), 121-6.
"Efficacy of an Antibiotic Coated Indwelling Catheter: A Preliminary Report", Sakamoto, I., Kanano, H., Nihira, H., Kitano, T., *Journal of Biomedical Materials Research*, vol. 19, 1031-1041, (1985).

*Primary Examiner*—Richard J. Apley
*Assistant Examiner*—Paul Prebilic

[57] ABSTRACT

Uniform adherent coatings of antimicrobial agents are applied to the surface of implants by applying a film of silicone oil to the surface of the implant and contacting the film-bearing surface with antimicrobial agents in a film-adherent form. A durable antimicrobial coating is formed. The coated implants can be packaged using mechanized implant handling equipment without significant loss of the antimicrobial coating. In a preferred embodiment a controlled-release implant for administering an anabolic agent is coated with a durable non-vulcanizing silicone fluid plus oxytetracycline hydrochloride coating which does not interfere with diffusion of the anabolic agent from the implant.

9 Claims, No Drawings

ANTIMICROBIAL COATED IMPLANTS

BACKGROUND AND SUMMARY OF THE INVENTION

This invention relates to improved implant devices. More particularly, this invention relates to an improvement in infection-resistant drug delivery implants. A silicone fluid is utilized to form a uniform implant-adherent coating of an antimicrobial agent. The coatings applied in accordance with this invention are better retained on the implant surface during mechanized implant packaging operations and are effective to prevent infection which may otherwise result after implantation of the device.

The use of controlled-release implants for administering estradiol to ruminant animals has been described in U.S. Pat. No. 4,191,741. During implantation of such implants, conditions are typically unsanitary, causing infection which can result in loss of implants. Use of an antibiotic or germicide layer or coating on the surface of the implant to reduce infections and to improve implant retention has been described in U.K. Pat. No. 2 136 688 A. The antibiotic coating facilitates parenteral administration of the implants under non-sterile conditions; requirements for claening the implant needle, the site of implantation on the animal, and the implantation device are minimized or eliminated. Other infection-resistant implant materials have been described. See, e.g. U.S. Pat. No. 4,581,028 disclosing infection-resistant materials suitable for use as vascular grafts prostheses or other implanted devices.

It is known that antimicrobial agents can be layered or coated onto the surface of an implant to inhibit infection at the site of implantation. However, some difficulties have been encountered in implementing that technology. Surface-applied antimicrobial agents have been found to be easily dislocated from the surface of the implant by nominal mechanical manipulation of the implants, for example, during automated packaging operations. Loss of the antimicrobial coating dramatically reduces resistance to infection. Labor intensive recoating procedures and manual methods of packaging the antimicrobial coated implants have been employed to assure that implants have effective antimicrobial coatings at the time of administration. Even with added care during the implant manufacturing/packaging process, coating uniformity is difficult to control.

Greater efficiencies in the manufacturing and packaging of implants as well as greater infection resistance at the implantation site would be realized with greater uniformity and implant-adherence of coatings of antimicrobial agents for implants. There is a need in the art for an improved method of coating implants to produce more uniform and more durable antimicrobial coatings on the implant surface, which exhibit good stability during manufacture, handling, and storage, which allow immediate availability of the antimicrobial agents upon implantation and which do not interfere with the function of the implant.

In accordance with the present invention, a silicone fluid is employed to promote uniform adhesion of antimicrobial agents to the surface of an implant. The invention yields many advantages for the production and use of infection resistant implants. Greater efficiencies in implant manufacturing and processing operations are possible. The adherent antimicrobial coating does not easily shake off the implant surface, allowing the implants to be subjected to the more rigorous conditions of automated packaging operations. Redusting or recoating procedures are eliminated. Because the use of present invention results in a more consistent and higher level application of antimicrobial agent, less quality control/analytical time is required during manufacturing operations. Further advantages include improved appearance of the implants and coating consistency. Application of the coating of antimicrobial agent is not affected by normal variations in raw materials.

The present invention is based on the discovery that a silicone fluid can be applied to the exterior surface of an implant to improve the adherence of subsequently applied antimicrobial agents. The silicone fluid has a high affinity for the implant surface and spreads on the surface of the implant to form a thin film. The film serves as a matrix-like carrier for subsequent applied antimicrobial agents, typically in a film-adherent powder or dust form. Antimicrobial agents contacting the silicone fluid layer are partially wetted by the fluid and retained on the surface of the implant.

In a preferred embodiment of the present invention an adherent antimicrobial coating is applied to an implant comprising an anabolic agent in a silicone polymer matrix adapted for sustained-release of the anabolic agent. The silicone fluid does not affect adversely either the safety or efficacy of the implant. The rate of diffusion of the anabolic agent from the implant remains essentially unchanged after coating in accordance with this invention.

It is, therefore, an object of this invention to provide an implant having an improved antimicrobial coating.

A further object of this invention is to provide an improved adherent and more uniform antimicrobial coating for implanted devices.

Still a further object of this invention is to provide a process for the economical application of adherent coatings of antimicrobial agents on implant surfaces.

DETAILED DESCRIPTION OF THE INVENTION

The improved implant coatings of this invention comprise a silicone fluid in contact with the surface of the implant and an antimicrobial agent in contact with the silicone fluid. The nature of the implant is not critical to the present invention, however the improved coatings are particularly suited for implants having surfaces formed from biocompatible silicone based polymers. The implants can assume any one of a variety of alternate constructions and can be used for prosthetic purposes or as reservoirs or matrices for the sustained release of biologically active compounds. They can be formed entirely of a silicone polymer, for examply by extrusion, molding and/or machining, or they can be fabricated by coating an implant core, constructed of an art-recognized biocompatible implant material or material composite, with a silicone polymer material.

Representative silicone polymers suitable for implant construction are diphenylpolysiloxane, dimethylpolysiloxane (dimethicone), phenylmethylpolysiloxane, trifluoropropylmethylsiloxane, polydimethylsiloxane copolymerized with polyethylene oxide, copolymers of dimethylpolysiloxane and polymethylmethacrylate and mixtures thereof.

Preferred implants which can be coated in accordance with this invention are those constructed in accordance with the disclosure of U.S. Pat. No 4,191,741 issued Mar. 4, 1980, the disclosure of which is expressly incorporated herein by reference. The implants described in that patent are designed for the controlled release administration of anabolic agents to ruminant animals. Exemplary of anabolic agents which can be released from such implants are estradiol, anabolic estradiol derivatives, including estradiol dipropanate, estradiol benzoate, estradiol valerate and the like, trenbolone acetate and certain resorcinol lactones including zeranol and zearalenone.

The improved antimicrobial coatings of this invention are applied to implant surfaces by first applying a silicone fluid to form a film in contact with the surface of the implant and subsequently contacting the film-bearing implant surfaces with an antimicrobial agent. Preferably the antimicrobial agent is in a film-adherent powder or dust form. The silicone film has a high affinity for the implant surface and for the antimicrobial agent and serves as a fluid matrix which wets and effectively binds the antimicrobial agent to the implant surface. The effectiveness of the silicone fluids for providing a base for the uniform adherent antimicrobial coatings of this invention derives from its high affinity both for the implant surface and for the antimicrobial agent itself.

Nonvulcanizing polydimethylsiloxane fluids and vulcanizing polydimethylsiloxane systems have been found to be especially suitable for use in forming the coatings in accordance with this invention. Such fluids are chemically equivalent to the silicone polymers from which the implants are preferably constructed. The silicone fluid therefore does not interfere with or affect implant safety or efficacy. Nor does it affect the availability of the antimicrobial agent at the implantation site.

Generally, the dimethylpolysiloxanes are low volatility liquids having a vicosity such that it will form thin silicone oil coating on the implant surfaces at ambient temperature. Preferred among the several commercially available silicone fluids is a high consistency medical grade fluid sold by Dow Corning Corporation under the designation 360 Medical Fluid. Dow Corning ® 360 Medical Fluid, a nonvulcanizing silicone fluid, is available in viscosities ranging from 20 centistokes to 12,500 centistokes (measured at 77° F.). Preferably the silicone fluid should have a viscosity range between about 200 and about 500 centistokes. A silicone fluid having a viscosity of about 350 centistokes has produced excellent results. Silicone oils with such viscosities exhibit a low volatility at room temperature and readily spread across the implant surface to form a thin fluid film in contact with the implant surface.

Implants can be coated with the polydimethylsiloxane liquid using art-recognized coating techniques such as by dipping or spraying. A coating pan can be used and offers advantages where a multiplicity of uniform implants are to be coated in a single batch. The silicone fluid is applied to the implant surface at a rate of about 0.1 to about 0.6 mg per $cm^2$ of implant surface. The optimum rate of application will depend on the viscosity of the applied fluid and the nature and condition of the implant surface. Where the silicone fluid has a viscosity of about 350 centistokes it is applied to the implant surface at a rate of about 0.2 to about 0.5 mg per $cm^2$ of implant surface. In a coating pan environment, the silicone fluid can be added to a batch of implants, for example cylindrical implants of uniform size, and will rapidly spread to cover the surfaces of the implants with a thin film of silicone fluid.

The silicone film bearing implants are then contacted with an antimicrobial agent having affinity for the silicon film. Preferably the antimicrobial agent is in the form of a dust or powder which when brought into contact with the film bearing implant surface is partially wetted by the fluid film and thereby effectively bound to the implant surface.

For the purpose of defining this invention, the term antimicrobial agent shall include antibiotic, antimicrobial, antibacterial, germicidal agents and the like. The antimicrobial coating may comprise a combination of antimicrobial agents. Typical antibiotics which may be used in this invention include: aminoglycosides, such as gentamicin, kanamycin, neomycin, paromomycin, streptomycin, or tobramycin; ansamycins, such as rifamycin, or rifampin; cephalosporins, such as cephalexin, cephaloridine, cephalothin, cefazolin, cephapirin, cephradine, or cephaloglycin; chloramphenicols; macrolides, such as erythromycin, tylosin, oleandomycin, or spiramycin; penicillins, such as penicillin G & V, phenethicillin, methicillin, oxacillin, cloxacillin, dicloxacillin, floxacillin, nafcillin, ampicillin, amoxicillin, or carbenicillin; suflonamides; tetracyclines, such as tetracycline, oxytetracycline, chlortetracycline, methacycline, demeclocycline, rolitetracycline, doxycycline, or minocycline; trimethoprim-sulfamethoxazole; polypeptides, such as bacitracin, polymyxins, tyrothricin, or vancomycin; and miscellaneous antibiotics, such as lincomycin, clindamycin, or spectinomycin. A preferred antibiotic is oxytetracycline hydrochloride (OTC).

Typical germicides which may be used in this invention include phenols; cresols; resorcinols; substituted phenols; aldehydes; benzoic acid; salicyclic acid; iodine; iodophors, such as betadine; chlorophors, such as hypochlorites; peroxides; such as hydrogen peroxide and zinc peroxide; heavy metals and their salts, such as merbromin, silver nitrate, zinc sulfate; surface-active agents, such as benzalkonium chloride; furan derivatives, such as nitrofurazone; sulfur and thiosulfates; salicylanilides; and carbanilides. Preferred germicides include betadine, iodine, silver nitrate and furan derivatives, such as nitrofurazone.

The amount of the antibiotic or germicide to be used to form the present coating varies with the nature of antibiotics or germicides employed and to some extent the method of coating application. For example, the amount of antibiotic can range from about 0.1 mg per $cm^2$ to about 2.1 mg per $cm^2$, with a preferred range being from about 0.2 mg to about 0.8 mg per $cm^2$. The typical range of the amount of germicide used is exemplified by betadine, which has a range of about 0.5 mg to about 5.2 mg per $cm^2$, and by nitrofurazone, which has a range of about 2.0 $\mu$g to about 8.3 $\mu$g per $cm^2$. The preferred ranges of betadine and nitrofurazone are: about 0.5 mg. to about 1.0 mg per $cm^2$; and about 2.1 $\mu$g to about 4.1 $\mu$g per $cm^2$, respectively. Effective amounts of oxytetracycline hydrochloride range from about 0.1 mg to 2.1 mg per $cm^2$, preferably from about 0.1 to about 1.0 mg per $cm^2$ and, more preferably, from about 0.14 to about 0.5 mg per $cm^2$.

Preferably, the antibiotic or germicide is in a particualte or powdered form ranging in particle size from about 325 mesh (45 $\mu$m) to about 60 mesh (250 $\mu$m) and more preferably from about 325 mesh (45 $\mu$m) to about 200 mesh (75 $\mu$m). Commercially available antibiotic powders can be milled to produce the desired particle size distribution.

EXAMPLE 1

COMPUDOSE 200® implants (24 mg. estradiol controlled-release implants, Elanco Products Company, a Division of Eli Lilly and Company) were used to evaluate applications of polydimethylsiloxane liquid based coatings of oxytetracycline hydrochloride (OTC). Evaluation results are summarized in Table 1. All implants were dusted in a coating pan with OTC at a rate of 2.5 mg OTC/implant. Predusting treatment was varied as follows: no pretreatment in Trials 1 and 2; pretreatment with 1% fumed silica (Aerosil®) in Trial 3; and pretreatment with Dow Corning® 360 Medical Fluid (viscosity=350 cs at 77° F.) for Trials 4–6.

TABLE 1
Oxytetracycline Hydrochloride Retention Results

| Trial | Pre-Dusting Treatment | Visual Observation of OTC Coating | Mean Value mg OTC/Implant | SD[2] |
|---|---|---|---|---|
| 1 | None | Uneven OTC Coating | — | — |
| 2 | None | Uneven OTC Coating | 0.8 | 0.19 |
| 3 | 1% Fumed Silica | Uneven OTC Coating | 0.8 | 0.41 |
| 4 | 2 mg of Silicone (Spray)/Implant | Very Even OTC Coating | 1.6 | 0.15 |
| 5 | 2 mg of Silicone (Spray)/Implant | Very Even OTC Coating | 2.7 | 0.19 |
| 6 | 2 mg of Silicone (Spray)/Implant (added to empty coating pan) followed by implants | Very Even OTC Coating | 1.8 | 0.31 |

[1]— indicates no values reported.
[2]Standard deviation from mean value.

The results demonstrate unequivocally the advantage offered by pretreatment of implants with a film-forming silicone fluid prior to dusting with antibiotic. It not only enhances the overall rate of retention of antibiotic on the implant surface, but it also enhances coating uniformity within the lots of coated implants. Moreover, visual inspection reveals an even coating and one that is retained during manipulation of the implants in automated packaging equipment utilizing vibratory bowls to align and distribute the implants into the individual package cavities.

EXAMPLE 2

Three successive lots of COMPUDOSE 200® Implants (approximately 26,000 implants, each) were coated in accordance with this invention. Treatment consisted of placing the implants in a coating or dusting pan and adding approximately 50 g of dimethicone (2 mg dimethicone/implant) followed by 65 g of oxytetracycline hydrochloride and tumbling until the implants appeared to be uniformly coated. For each of the three lots, implants were randomly selected, packaged, and submitted for evaluation. The results are summarized in Table 2.

TABLE 2
OTC Retention on COMPUDOSE 200® Implants

| | mg OTC/Implant[1] |
|---|---|
| Lot 1 | 1.64 |
| Lot 2 | 1.61 |
| Lot 3 | 1.52 |

[1]Mean value of 10 implants

We claim:

1. An implant adapted for the controlled release of an anabolic agent, said implant comprising a silicone polymer matrix, an anabolic agent in said polymer matrix, and an antimicrobial coating, wherein the coating comprises a first-applied non-vulcanizing silicone fluid and a subsequently applied antimicrobial agent in contact with said fluid.

2. The implant of claim 1 wherein the anabolic agent is selected from the group consisting of anabolic steroids.

3. The implant of claim 1 wherein the anabolic agent is estradiol.

4. The implant of claim 1 wherein the antimicrobial agent is selected from the group consisting of antibiotics and germicides.

5. The implant of claim 1 wherein the antimicrobial agent is oxytetracycline hydrochloride.

6. The implant of claim 1 wherein the silicone polymer matrix and anabolic agent form a coating surrounding a biocompatible inert core.

7. The implant of claim 6 wherein the anabolic agent is estradiol.

8. The implant of claim 7 wherein the silicone fluid has a viscosity of about 200 to about 500 centistokes and the antimicrobial agent is oxytetracycline hydrochloride.

9. In an implant adapted for the controlled release of an anabolic agent, said implant comprising an anabolic agent in a silicone polymer matrix and an antimicrobial coating on the surface of said implant, the improvement wherein the antimicrobial coating comprises a first-applied non-vulcanizing silicone fluid in contact with the surface of said implant and a subsequently applied antimicrobial agent in contact with said silicone fluid.

* * * * *